(12) United States Patent
Santilli (10) Patent No.: US 6,673,075 B2
(45) Date of Patent: Jan. 6, 2004

(54) POROUS INTERVERTEBRAL SPACER

(76) Inventor: Albert N. Santilli, 28326 Gates Mills Blvd., Pepper Pike, OH (US) 44124

(*) Notice: Subject to any disclaimer, the term of this patent is extended or adjusted under 35 U.S.C. 154(b) by 60 days.

(21) Appl. No.: 10/004,916

(22) Filed: Dec. 3, 2001

(65) Prior Publication Data

US 2002/0120336 A1 Aug. 29, 2002

Related U.S. Application Data

(63) Continuation-in-part of application No. 09/792,694, filed on Feb. 23, 2001.

(51) Int. Cl.$^7$ .............................................. A61B 17/56
(52) U.S. Cl. .................... 606/61; 623/17.16; 623/23.51
(58) Field of Search ............................ 606/61, 70, 69, 606/72, 71, 60; 623/17.16, 17.11, 11.11, 23.56, 16.11, 23.51

(56) References Cited

U.S. PATENT DOCUMENTS

| | | |
|---|---|---|
| 3,855,638 A | 12/1974 | Pilliar |
| 3,906,550 A | 9/1975 | Rostoker et al. |
| 4,429,691 A | 2/1984 | Niwa et al. |
| 4,542,539 A | 9/1985 | Rowe, Jr. et al. |
| 4,693,721 A | 9/1987 | Ducheyne |
| 4,714,469 A | 12/1987 | Kenna |
| 4,743,256 A | 5/1988 | Brantigan |
| 4,878,915 A | 11/1989 | Brantigan |
| 5,071,437 A | 12/1991 | Steffee |
| 5,171,281 A | 12/1992 | Parsons et al. |
| 5,192,326 A | 3/1993 | Bao et al. |
| 5,201,766 A | 4/1993 | Georgette |
| 5,222,983 A | 6/1993 | Schmitz et al. |
| 5,306,309 A | 4/1994 | Wagner et al. |
| 5,314,478 A | 5/1994 | Oka et al. |
| 5,382,248 A | 1/1995 | Jacobson et al. |
| 5,458,638 A | 10/1995 | Kuslich et al. |
| 5,458,643 A | 10/1995 | Oka et al. |

(List continued on next page.)

OTHER PUBLICATIONS

Collis, et al, Anterior Disc Total Replacement: A Modified Anterior Lumbar Interbody Fusion., Aspen Publications (1989) pp. 149–152.

Wheeler, et al., Porous Litanium Alloy for Prosthesis Attachment, Titatnium Alloys in Surgical Implants (1983) pp. 241–153.

Primary Examiner—Pedro Philogene
(74) Attorney, Agent, or Firm—Rankin, Hill, Porter & Clark LLP (57) ABSTRACT

An intervertebral spacer suitable for use as a spinal implant includes a rigid, porous body made of a biocompatible material. The body is strong enough to accommodate loads imposed by adjacent vertebrae and is porous enough to facilitate tissue ingrowth and bony fusion. The porosity is provided by a plurality of randomly sized, substantially interconnected voids disposed throughout the body. The spacer can be manufactured by a variety of techniques. In one technique, a plurality of polymer pellets are placed in a mold of a desired shape and heated to melting or near-melting temperature. The pellets are fused together to form a porous, rigid structure. In another technique, tortuous strands of a biologically inert material are intermixed with each other and are sintered into a desired shape in a mold. The spacer also can be made of a sintered mixture of strands and pellets of a biologically inert material. The material for the strands and the pellets typically is titanium or a titanium alloy, although other metals and certain polymers such as PEEK can be used. In another techniques, the spacer is made of void-containing foam metal, void-containing powdered metal, or void-containing ceramic. The spacer also can be made from a solid block of a biocompatible material by drilling or machining a plurality of interconnected openings that extend through the block. The spacer can be provided in a variety of shapes to suit the needs of individual patients.

27 Claims, 4 Drawing Sheets

U.S. PATENT DOCUMENTS

| | | |
|---|---|---|
| 5,514,180 A | 5/1996 | Heggeness et al. |
| 5,522,899 A | 6/1996 | Michelson |
| 5,534,030 A | 7/1996 | Navarro et al. |
| 5,545,229 A | 8/1996 | Parsons et al. |
| 5,562,738 A | 10/1996 | Boyd et al. |
| 5,571,192 A | 11/1996 | Schonhoffer |
| 5,593,409 A | 1/1997 | Michelson |
| 5,609,635 A | 3/1997 | Michelson |
| 5,611,800 A | 3/1997 | Davis et al. |
| 5,665,119 A | 9/1997 | Koller |
| 5,961,554 A * | 10/1999 | Janson et al. .................. 606/61 |
| 6,039,762 A | 3/2000 | McKay |
| 6,083,264 A | 7/2000 | Wood et al. |
| 6,086,613 A | 7/2000 | Camino et al. |
| 6,093,205 A | 7/2000 | McLeod et al. |
| 6,096,080 A * | 8/2000 | Nicholson et al. ........ 623/17.16 |
| 6,102,948 A | 8/2000 | Brosnahan, III |
| 6,113,638 A * | 9/2000 | Williams et al. ............. 128/898 |
| 6,126,689 A * | 10/2000 | Brett ......................... 623/17.15 |
| 6,149,688 A * | 11/2000 | Brosnahan et al. ......... 623/23.5 |
| 6,283,997 B1 * | 9/2001 | Garg et al. ............... 623/16.11 |
| 6,371,988 B1 * | 4/2002 | Pafford et al. ................. 606/61 |

* cited by examiner

POROUS INTERVERTEBRAL SPACER

REFERENCE TO RELATED PATENT APPLICATION

This application is a continuation-in-part of application Ser. No. 09/792,694, filed Feb. 23, 2001 by Albert N. Santilli (the "Cage Plate Patent"), the disclosure of which is incorporated herein by reference and from which priority is claimed, and a continuation-in-part of application Ser. No. 09/679,014, filed Oct. 4, 2000.

REFERENCE TO RELATED PATENT

Reference is made to U.S. Pat. No. 5,961,554, issued Oct. 5, 1999 to Frank S. Janson and Albert N. Santilli (the "Titanium Bead Spacer Patent"), the disclosure of which is incorporated herein by reference.

BACKGROUND OF THE INVENTION

1. Field of the Invention

The invention relates to an intervertebral spacer useful for spinal surgery and, more particularly, to a porous, strong intervertebral spacer formed of a biologically inert material.

2. Description of the Prior Art

Techniques and devices for fusing two or more vertebrae of the spine together are well known. Such techniques are commonly performed to correct problems, such as chronic back pain, which result from degenerated intervertebral discs. One technique for fusing together two or more vertebrae of the lumbar spine includes excising a portion of the disc between adjacent vertebrae and inserting one or more portions of an intervertebral spacer of a desired shape between the adjacent vertebrae. The intervertebral spacer may be inserted by either an anterior or posterior approach to the spinal column depending on a number of factors, including the number of vertebrae to be fused and past operative procedures. Upon healing, the vertebrae are desirably fused together through the intervertebral spacer.

Intervertebral spacers have been described by a number of names, including spinal implants and spinal cages. For convenience, all such devices will be referred to herein as "intervertebral spacers."

Conventionally, intervertebral spacers have been autogenic bone harvested from other areas of the body, such as the pelvis, allogenic bone taken from cadavers or xenogenic bone, such as bovine bone sections. However, the use of bone grafts can add complications to the fusion procedure. For example, when using an autogenic bone graft, a second incision must be made in the patient to harvest the additional bone to be used in the graft, thus increasing the pain and blood loss to the patient. When allogenic or xenogenic bone grafts are used there is a potential for the transmission of disease from the cadaver or other graft source to the patient.

The use of non-biological implants, such as carbon fiber spacers, also has been attempted in the past, but these spacers tend to lack sufficient porosity and tissue ingrowth characteristics to function adequately. It would be desirable to provide a non-biological spacer which is non-reactive in the body and which has the strength and tissue ingrowth characteristics of a bone graft spacer.

SUMMARY OF THE INVENTION

In view of the aforementioned needs, the present invention provides a new and improved porous intervertebral spacer that can be used in the same manner as a bone graft spacer to fuse vertebrae together. The Titanium Bead Spacer Patent discloses and claims a porous intervertebral spacer composed of titanium beads formed by sintering the beads together into a porous shape in a mold of a desired shape and size. The Cage Plate Patent discloses a plate to which a cage, or spacer, is attached. The spacer is composed of a variety of materials that are worked on in a variety of ways. The present invention relates to a porous intervertebral spacer per se, including materials from which the spacer can be made and various techniques for forming the spacer.

In general, the intervertebral spacer according to the invention is made of a biocompatible material that has enough strength to adequately support adjacent vertebral bodies and that is porous enough to permit tissue ingrowth and bony fusion. The spacer comprises a rigid, porous body that includes a plurality of randomly sized, substantially interconnected voids that provide porosity throughout the body. Desirably, the spacer contains solid material within the range of about 45 to 75 percent of the total volume of the spacer; thus, the spacer has a porosity within the range of 25 to 55 percent.

In accordance with one technique for manufacturing the spacer according to the invention, the spacer is comprised of polymer pellets. The pellets are fused together in a mold of a desired shape. The size of the pellets determines the porosity of the finished spacer. In certain applications it may be desirable to mix pellets of various sizes to obtain a finished spacer having a variable porosity. Desirably the pellets are spherical beads made of PEEK (polyaryl, ether, ether ketone) resin that occupy a range of 45 to 75 percent of the volume of the spacer.

In another technique, the spacer is made of a plurality of strands of a biologically inert material. A porous metallic fiber mesh is formed by interengaging and intertwining the strands, which then are sintered together into a porous, rigid shape.

In accordance with another technique, the spacer is comprised of pellets that are intermixed with a plurality of strands of a biologically inert material. The pellets and the strands are sized such that they yield, when fused, a spacer with the fused pellets and strands occupying a range of 45 to 75 percent of the volume of the spacer. Strands of wire mesh, preferably titanium or titanium alloy, are intermixed with titanium or titanium alloy pellets to form a spacer having variable qualities of strength and porosity. The strands and the pellets also can be made of other biocompatible metals or a strong, biologically inert polymer such as PEEK.

In accordance with yet another technique, the spacer is comprised of void-containing foam metal. In this technique, the spacer is formed by mixing a blowing agent with powdered metal, heating the mixture to foaming temperature, and cooling the metal. The resulting product contains numerous interconnected pores of different sizes and shapes.

In accordance with yet another technique, the spacer is comprised of void-containing powdered metal. In this technique, the spacer is formed by filling a mold with a uniform mixture of (1) beads made of wax or other suitable low melting temperature material, (2) powdered metal, and (3) a binder. The mold is heated to a low temperature to set the binder and melt the beads and thereby remove them. Thereafter, the mold is heated to a high, sintering temperature to oxidize the binder and solidify the powder into a porous shape.

In accordance with yet another technique, the spacer is comprised of void-containing ceramic materials such as alumina or silica or combinations of ceramic materials. The spacer can be formed as described previously, for example, by mixing ceramic powders with foaming agents and heating the mixture to a temperature adequate to form interconnected voids and sinter the ceramic ingredients.

Yet an additional technique for forming the spacer according to the invention is to take a solid block of a biologically inert, strong material such as PEEK polymer, titanium, or ceramic, the block being shaped as desired by the surgeon, and to drill or otherwise form a series of openings or bores in the block. Such openings or bores could be formed by EDM, chemical attack, or any other known machining technique. Preferably, the openings or bores are variably sized and variably spaced, and will intersect at numerous, randomly located places within the spacer so as to permit and promote tissue ingrowth and bony fusion.

In all of the other embodiments disclosed herein, the spacer can be formed in a variety of shapes such as a prism (for example, a rectangular prism), a cylinder, or a plate. A particularly desirable shape is a body defined by spaced, parallel, top and bottom faces, the top and bottom faces being of the same size and shape; a pair of spaced, parallel side walls; a first, flat, end wall; and a second, curved end wall, the second end wall being curved along a radius extending between the spaced side walls, the radius approximating the anterior portion of a vertebral body. The body of the spacer can be provided with through bores and external ribs, fins, or notches for various purposes.

The foregoing and other features and advantages of the invention are fully described hereinafter. The accompanying drawings constitute a part of the specification and illustrate an exemplary embodiment of the invention.

DESCRIPTION OF THE PREFERRED EMBODIMENT

Figure 1:
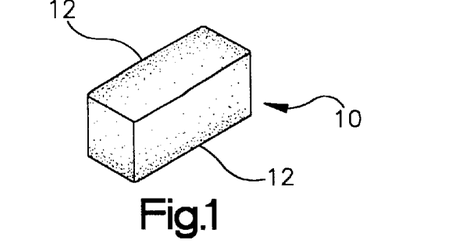
FIG. 1 is a perspective view of an intervertebral spacer in accordance with the invention, the spacer being in the form of a rectangular prism made of fused beads.
Figure 7:
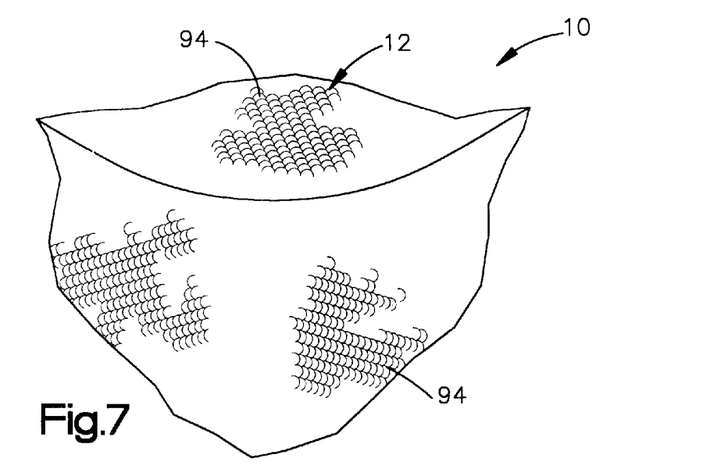
FIG. 7 is an enlarged view of the surface of the spacer of FIG. 1.
Figure 8:
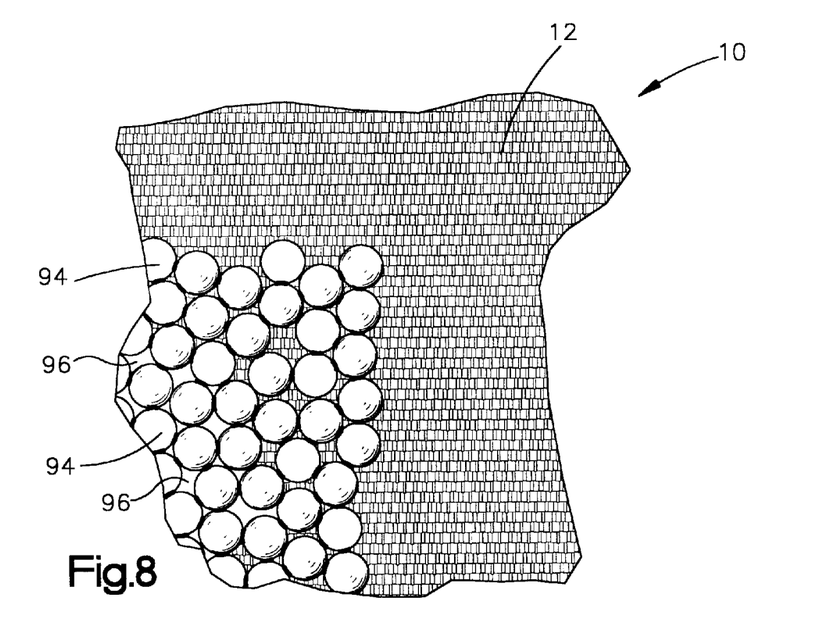
FIG. 8 is a view similar to FIG. 7 showing the surface enlarged to an even greater extent.

With reference to the drawings and initially to FIGS. 1, 7, and 8, there is shown an intervertebral spacer 10 in accordance with the present invention. The spacer 10 is in the form of a porous biologically inert block in the form of a rectangular prism. The corners and edges of the spacer 10 may be formed with a small radius if desired. One or more such rectangular, block-shaped spacers 10 are sized to fit within an opening or graft bed formed between adjacent vertebrae by the surgical excision of a portion of the intervertebral disc and confronting portions of the adjacent vertebral bodies. The particular size of the spacer 10 will be determined by the particular vertebrae to be fused, and condition of the vertebrae. Advantageously, because the spacers are not made of a biological material, they are easily stored and can be manufactured in a variety of shapes and sizes to accommodate anticipated situations.

The procedure for fusing two or more vertebrae together using the spacer 10 of the invention is substantially the same as the procedure for fusing vertebrae using a bone graft, but without many of the complications due to obtaining a suitable bone graft and the possibility of transmitting disease from the bone graft donor. One anterior procedure for implanting a bone graft to fuse vertebra of the lumbar spine is discussed in Collis et al., "Anterior Total Disc Replacement: A Modified Anterior Lumbar Interbody Fusion," Lumbar Interbody Fusion, ed. Robert Watkins, Chapter 13, pp. 149–152, Aspen Publications (1989), the disclosure of which is incorporated herein by reference.

Figures 2, 3:
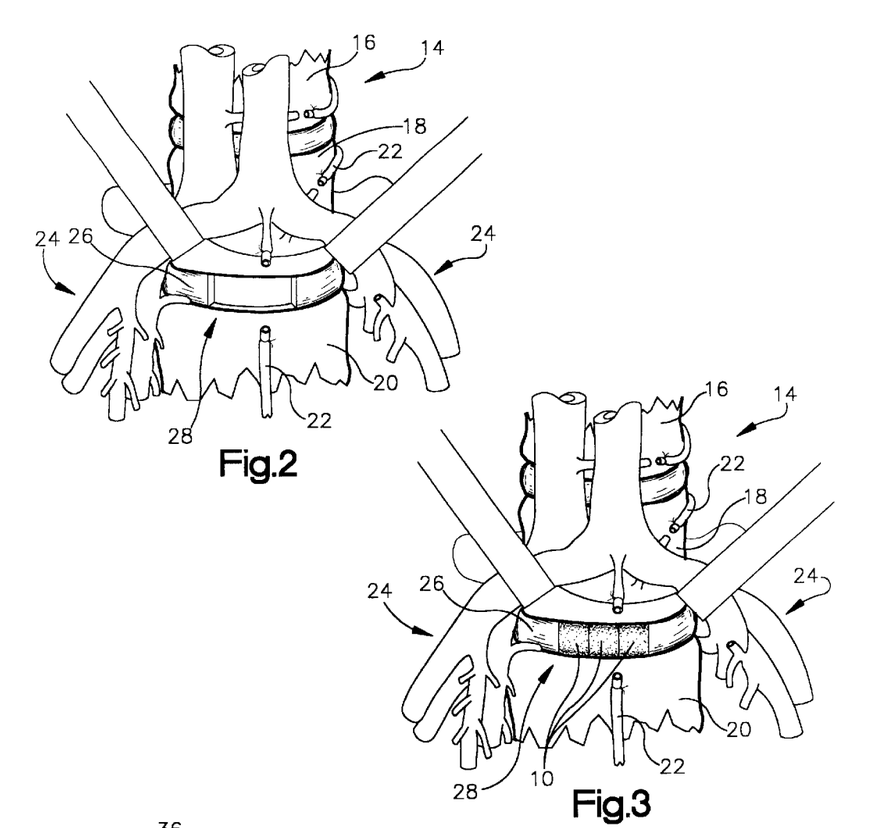
FIG. 2 is an elevational view of the anterior of a portion of the lumbar spine and sacrum illustrating a graft bed.
FIG. 3 is a view similar to FIG. 2 showing three spacers according to FIG. 1 implanted in the graft bed.

Referring to FIGS. 2 and 3, there is shown an anterior elevation view of the lumbar spine 14 including the fourth and fifth lumbar vertebrae 16, 18, respectively, and the sacrum 20 with the sacral vessels 22 ligated and both iliac vessels 24 retracted outwardly to expose the vertebral disc 26 between the fifth lumbar vertebra 18 and the sacrum 20. As an example, to fuse the fifth lumbar vertebra 18 to the sacrum 20, using an anterior approach, a graft bed 28 is prepared by surgically exposing the affected area and excising portions of the vertebral body of the vertebra 18 and the sacrum 20 and the section of the disc 24 located therebetween, as shown in FIG. 2. An appropriate number of spacers 10, in this example, three, are then implanted into the graft bed 28. Over time bony tissue ingrowth will desirably fuse the vertebral bodies of the vertebra 18 and the sacrum 20 to the spacers 1f0 and thus fuse the vertebra to the sacrum through the spacers. The number of spacers 10 employed will be a function of a number of factors, including the particular vertebrae to be fused and the deterioration of the vertebral disc and of the vertebral bodies themselves.

Figure 4:
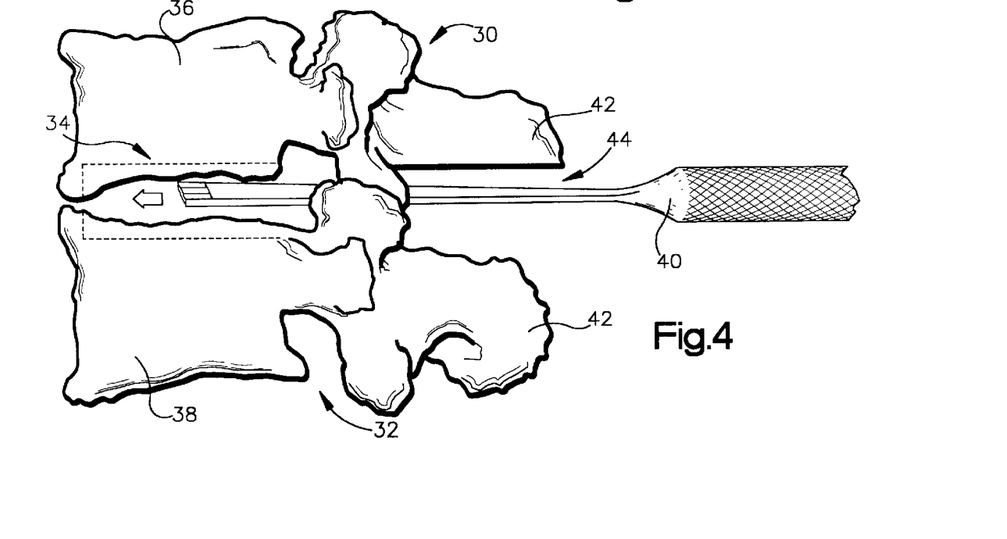
FIG. 4 is a side elevational view of two representative lumbar vertebrae illustrating the location of a posterior-formed graft bed.
Figure 5:
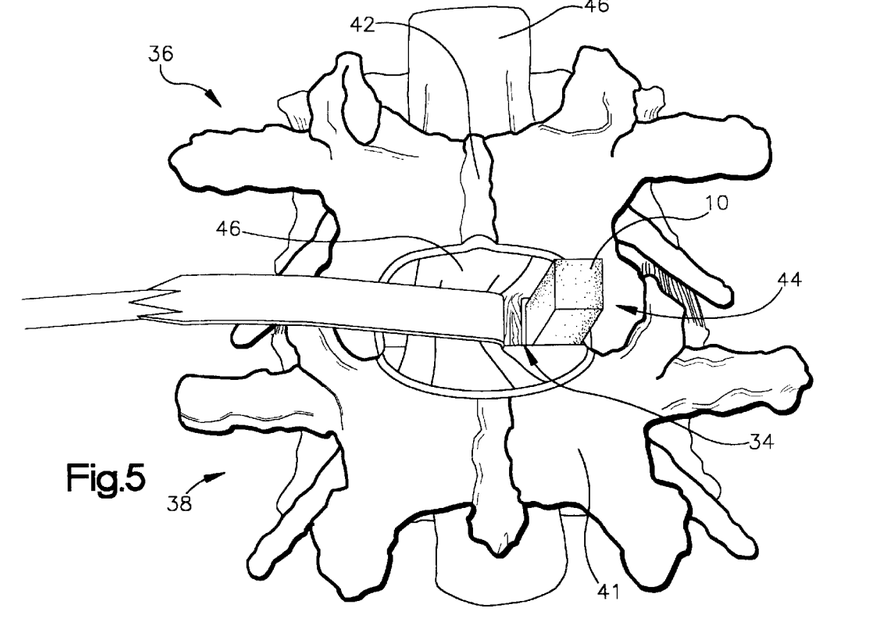
FIG. 5 is an elevational view of the posterior of representative lumbar vertebrae illustrating a spacer according to FIG. 1 being implanted into one of two separate posteriorly formed graft beds.
Figure 6:
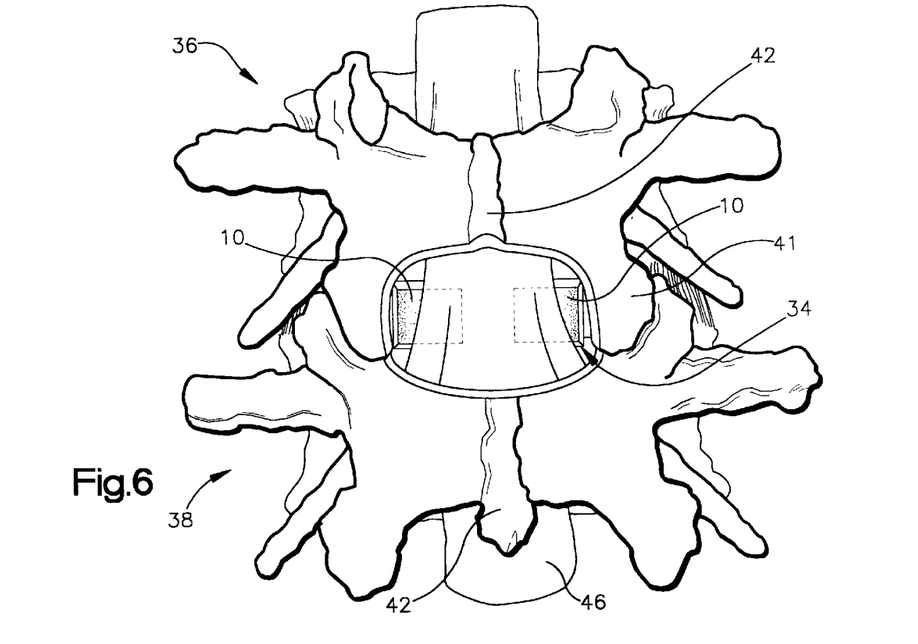
FIG. 6 is a view similar to FIG. 5 showing two spacers according to FIG. 1 implanted in the graft beds.

The intervertebral spacers 10 may also be implanted through known posterior approaches. In a typical procedure using a posterior approach in which two spacers are implanted, such as is shown in FIGS. 4 through 6 which represent side and rear elevations of two representative lumbar vertebrae 30, 32, the posterior portion of the subject area of the lumbar spine is surgically exposed. Graft beds 34 are then formed by excising the required portions of adjacent vertebral bodies 36, 38 of the vertebrae 30, 32, respectively, and a section of the disc located therebetween. The graft beds 34 may be formed using a cutting tool 40, such as is shown in FIG. 4 (FIG. 4 omits the Canda Equina and the disc for clarity), wherein portions of the lamina 41 and/or spinous process 42 of one or both of the vertebrae are removed to open a passage 44 through which the tool may be inserted to reach the vertebral bodies. To implant the spacers 10 once the graft beds 34 have been formed, the Canda Equina and protective dura 46 are first retracted to one side to expose a graft bed and a spacer is inserted into the exposed graft bed (see FIG. 5), and then the Canda Equina and dura are retracted to the other side to insert a spacer into the exposed other graft bed.

A typical spacer 10 for fusing vertebrae of the lumbar spine may be from 10 to 13 millimeters in width, 12 to 18 millimeters in height, and 25 to 30 millimeters in length. A typical size is 10 mm wide, 27 mm long, and a variable height of 12, 14, 16 or 18 mm. The spacer 10 can be provided in shorter lengths of 24 mm, or longer lengths of 30 mm. The spacer 10 also can be provided in the different widths, for example, 13 mm.

With a width of 13 mm, variable lengths of 24, 27 or 30 can be provided. The height also can be selected among 12, 14, 16 or 18 mm.

It will be appreciated that while the specific example of the intervertebral spacer described herein is with reference to a spacer for fusing vertebrae of the lumbar spine together or to the sacrum, the invention applies also to spacers for fusing vertebrae of the cervical or thoracic spine as well. The particular shape of the spacer is also a function of the application. While a generally rectangular spacer is well suited to fusing lumbar vertebrae, in other instances other shapes for the spacer, such as cylindrical, may be desirable. Reference is made to the Titanium Bead Spacer Patent and to the description that follows for a description of a variety of suitable shapes. Moreover, it will be recognized that the spacers of the invention also may be used in other areas of the body to fuse bone together where necessary.

Referring to FIG. 8, in a manner analogous to the spacer disclosed in the Titanium Bead Spacer Patent, the spacer 10 may be composed of biologically inert pellets 94 that preferably are in the form of spherical beads. It will be appreciated that a variety of pellet shapes can be used, but a spherical shape is preferred. The pellets 94 have a diameter such they occupy generally 45 to 75 percent of the volume of the spacer 10. The interstices between and among the pellets 94 are indicated by the reference numeral 96. The interstices 96 occupy generally 25 to 55 percent of the volume of the spacer 10. The foregoing proportions provide a spacer 10 that is sufficiently porous throughout to allow for the flow of bodily fluids through the spacer 10 and to promote tissue ingrowth and bony fusion with adjacent vertebrae. The pellets 94 also result in porous surfaces 12 over the spacer 10 which, when implanted, develop a high friction interface with the contacting vertebral bodies to facilitate maintaining the spacer 10 in place.

The pellets 94 preferably are made of PEEK (polyaryl, ether, ether ketone) resin which is believed to be non-reactive within the body. PEEK polymer is a high performance thermoplastic polymer made by Victrex pic of Westchester, Pa. PEEK polymer is semi-crystalline and is insoluble in all common solvents and has excellent resistance to a wide range of organic and inorganic liquids. The polymer retains excellent mechanical properties up to 572° F. It also can resist high dose levels of gamma radiation. It is an excellent choice for spinal implants and similar applications because it has a low value of coefficient of linear thermal expansion ($2.6 \times 10^{-5}$° F. by ASTM D696) up to the high glass transition temperature of 289° F. ($T_g$ by DSC).

As disclosed in the Titanium Bead Spacer Patent, the pellets 94 also can be made of titanium or a titanium alloy (such as Ti-6Al-4V) which is non-reactive within the body. Since the early 1970's, titanium and titanium alloys have been approved by the United States Food and Drug Administration for use in knee, shoulder, and hip implants to promote bone ingrowth. It also is possible to use other metals for the pellets 94, provided such metals are biocompatible. Such metals include cobalt-chromium alloys, tantalum, niobium, alloys of these metals, and possibly stainless steel.

It has been found that pellets 94 of a certain size range are preferred. Suitable small pellets 94 will have a mesh size of −45 +60 (0.009 inch to 0.011 inch). Suitable medium pellets 94 will have a mesh size of −25 +30 (0.016 inch to 0.027 inch). Suitable large pellets 94 will have a mesh size of −18 +30 (0.032 to 0.046 inch). The size of the pellets 94 determines the porosity of the finished spacer 10. The larger the pellets 94, the greater the porosity. In certain applications, it may be desirable to mix pellets 94 of various sizes to obtain a finished spacer 10 having a variable porosity.

The spacer 10 can be manufactured by a second technique. In the second technique, the spacer 10 is made of a plurality of fibers or strands that form a mesh. Titanium mesh presently is used as a porous coating for knee, shoulder, and hip implants. Such mesh sometimes is referred to a spaghetti mesh, and is commercially available from the Zimmer Company of Warsaw, Ind. Reference is made to U.S. Pat. Nos. 3,906,550; 4,693,721; and 5,665,119, the disclosures of which are incorporated herein by reference, for a discussion of the use of metal fiber as a porous bone structure material.

The spacer 10 can be manufactured by a third technique. In the third technique, the spacer 10 is made of a mixture of strands and pellets. If desired, the strands and the pellets could be made of titanium, titanium alloy, or a strong, non-reactive polymer such as PEEK. This spacer 10 has variable qualities of strength and porosity. In general, the use of a mixture of strands and pellets results in a stronger, less porous spacer 10.

In order to maintain the structural integrity of each embodiment of the spacer 10, the pellets, the strands, or the combination of pellets and strands must be fused together. One method of fusing PEEK pellets to form the spacer 10 includes placing the pellets into a cavity within a mold (not shown). The mold preferably is a three-piece mold forming a cavity of the finished dimensions of the spacer 10. The mold containing the PEEK pellets then is heated to a temperature high enough to cause sintering to occur. Other methods for fusing PEEK pellets or strands which provide a sufficiently strong spacer 10 also may be acceptable. When PEEK strands are used to form the spacer 10, the strands are placed in the mold in a tangled, tortuous mass. Sintering produces strong inter-strand bonds with variably sized openings to form a spacer 10 of suitable strength and porosity.

When sintering titanium or titanium alloy strands or pellets to form the spacer 10, the mold preferably is a substantially purified graphite mold. The mold is heated to a high temperature, for example, 2000 degrees F. or higher, until the sintering is complete, around 24 hours. Other conventional methods for fusing titanium which provide a sufficiently strong spacer 10 also may be acceptable. When titanium spaghetti mesh is used to form the spacer 10, the strands are placed in the mold in a tangled, tortuous mass. Sintering produces strong inter-strand bonds with variably sized openings to form a spacer 10 of suitable strength and porosity.

The spacer 10 can be manufactured by a fourth technique. In this technique, the spacer 10 is made of foam metal that contains a plurality of interconnected voids. Foam metal, produced by mixing a powdered foaming agent with a metal powder, is a porous metal matrix with unique properties. One technique for forming foam metal is commonly known as "free-foaming." During free-foaming, a billet of metal containing a foaming agent is placed in a furnace and is heated to temperatures greater than the matrix metal. As the billet melts, the foaming agent releases gas in a controlled way. The gas discharge slowly expands the metal as a semi-sold foamy mass. The foaming process stops as the metal cools. Density is controlled by changing the foaming agent content and varying the heating conditions. U.S. Pat. No. 5,151,246, the disclosure of which is incorporated herein by reference, discloses a suitable technique for the manufacture of foam metal that could be used to produce the spacer 10 of the present invention.

Another technique for forming form metal is to mix a small quantity of powdered foaming agent with conventional metal powders to form a billet. The billet is heated by induction coils to a foaming temperature. The now-liquid billet is injected in a foaming state into complex molds. The injection of molten foam provides a versatile way to produce complex shapes of foam metal and can be utilized to produce a spacer 10 with non-uniform geometries.

The spacer 10 can be manufactured by a fifth technique. In this technique, the spacer 10 is made of powdered metal that contains a plurality of interconnected voids. Powdered metal is produced by compressing and sintering various powdered metals. In conventional powdered metal technology, metal powder is compressed using accurately formed dies and punches in special types of hydraulic or mechanical presses. The compressed pieces then are sintered in an atmosphere-controlled furnace at high temperature to cause the metal particles to be bonded together metallurgically. A subsequent sizing or coining operation and a supplementary heat treatment may be employed. Powdered metals may be used to form irregularly curved or eccentrically shaped pieces.

The spacer 10 can be made of powdered metal in a lost wax type of process. By this process, a mold is filled with a uniform mixture of wax beads, powdered metal and a low temperature binder. The mixture is compressed so that the mold is packed with the mixture. The mold then is heated to a first, relatively low, temperature to set the binder and melt the wax. Thereafter, the mixture is heated to a second, relatively high, sintering temperature to oxidize the binder and sinter the powder.

In accordance with a sixth technique for making the spacer 10, the spacer 10 is comprised of void-containing ceramic materials such as alumina or silica or combinations of ceramic materials. Reference is made to U.S. Pat. No. 6,039,762, the disclosure of which is incorporated herein by reference, for a description of suitable ceramic materials. The spacer can be formed as described previously, for example, by mixing ceramic powders with foaming agents and heating the mixture to a temperature adequate to form interconnected voids and sinter the ceramic ingredients.

A seventh technique for forming the spacer 10 is to take a solid block of a biologically inert, strong material such as PEEK polymer, titanium, or ceramic, the block being is a shape desired by the surgeon, and to drill or otherwise form a series of openings or bores in the block. Such openings or bores could be formed by EDM, chemical attack, or any other known machining technique such as mechanical drilling, laser drilling, water jet drilling, or plasma jet drilling. Preferably, the openings or bores are variably sized and variably spaced, and will intersect at numerous, randomly located places within the spacer so as to permit and promote tissue ingrowth and bony fusion.

Referring now to FIGS. 9–12, particularly desirable shapes for the spacer according to the invention are shown. The shapes shown in FIGS. 9–12 are in addition to the shapes disclosed in the Cage Plate Patent and the Titanium Bead Spacer Patent. Regardless of the external shape of the spacer, it should be made of one of the materials or combination of materials discussed above, and it should be manufactured according to one of the manufacturing techniques discussed above.

Figure 9:
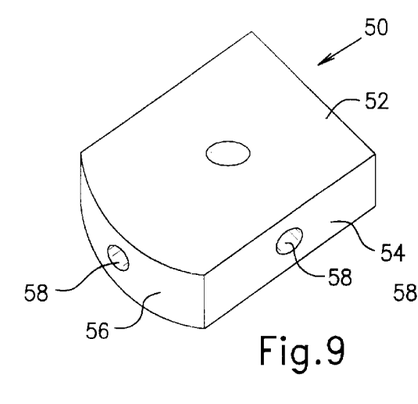
FIGS. 9–12 are perspective views of spacers according to the invention, showing a variety of shapes in which the spacers can be provided.

With specific reference to FIG. 9, a spacer according to the invention is indicated by the reference numeral 50 and includes a top wall 52, a bottom wall (not shown) that is the same size and shape as the top wall 52, first and second side walls 54 (only one of which is shown), a first end wall (not shown), and a second end wall 56. The spacer 50 includes through bores 58 that intersect at the center of the spacer 50. If desired, the top and bottom walls could be tapered from a larger dimension adjacent the second end wall 56 to a smaller dimension adjacent the first end wall. The amount of the taper is dependent on the shape of the patient's spine at that location where the spacer 50 is to be implanted. Preferably, the top and bottom walls, the side walls, and the first end wall are flat in order to snugly fit within the space in the patient's spine that will be formed by the surgeon. The second end wall 56 is curved from one side wall 54 to the other along a radius that approximates the radius of a vertebral body. If desired, the second end wall 56 also could be curved from the top wall 52 to the bottom wall, in which case the second curvature should approximate a radius extending between adjacent vertebral bodies. This second curvature could be convex or concave depending on the curvature of the spine at that location where the spacer is to be implanted. The bores 58 promote tissue ingrowth and bony fusion, and also can be of assistance to the surgeon during the installation process. The bores 58 preferably are circular (because it is easier to form a cylindrical bore), although non-circular shapes such as ellipses can be used, if desired.

Figure 10:
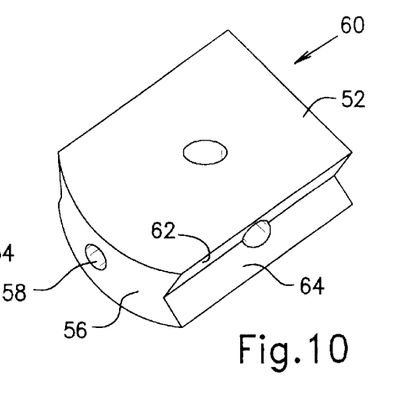

Referring now to FIG. 10, a spacer according to the invention is indicated by the reference numeral 60. The spacer 60 is identical to the spacer 50 except that the side walls 54 are notched along their length. The notches are defined by two panels 62, 64, each preferably of the same size and shape. The included angle between the panels 62, 64 can be anywhere within the range from 0 to 90 degrees. The use of notched side walls 54 provides additional support for the spacer 60 to resist vertical loads during the spinal fusion process (which can take weeks or months).

Figure 11:
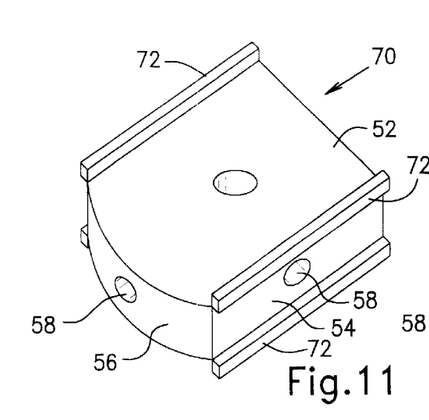

Referring now to FIG. 11, another spacer according to the invention is indicated by the reference numeral 70. The spacer 70 is identical to the spacer 50 except that the boundaries between the top, bottom, and side walls is defined by longitudinally extending fins 72. The fins 72 can be provided in a variety of cross-sectional shapes, including round, square, rectangular, and triangular. As with the notched side walls 54 of the spacer 60, the fins 72 provide additional support for the spacer 70 to resist vertical loads during the spinal fusion process.

Figure 12:
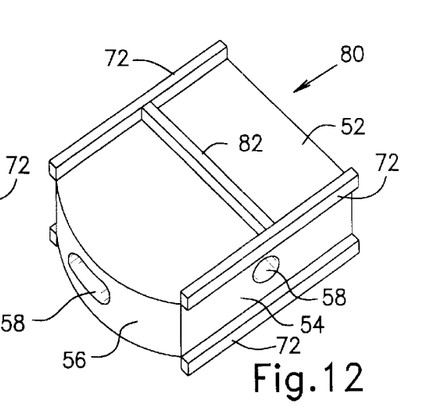

Referring now to FIG. 12, another spacer according to the invention is indicated by the reference numeral 80. The spacer 80 is identical to the spacer 70 with certain exceptions. First, the bore 58 that opens through the top wall 52 and the bottom wall has been eliminated. Second, a laterally extending rib 82 extends from one side wall 54 to the other side wall 54 at approximately the mid-point of the spacer 80 on both the top wall 52 and the bottom wall. Third, the longitudinally extending bore 58 is elliptical rather than circular. The ribs 82 can be provided in a variety of cross-sectional shapes, including round, square, rectangular, and triangular, although triangular is preferred. The ribs 82 provide additional support for the spacer 80 to resist horizontal loads during the spinal fusion process As will be appreciated from the foregoing description, an intervertebral spacer according to the invention is made of a biologically inert material that has enough strength to adequately support adjacent vertebral bodies and that is porous enough to permit tissue ingrowth and bony fusion. The spacer can be made from a variety of materials in a variety of manufacturing processes. The spacer also can be provided in a variety of shapes to suit the needs of a wide range of patients.

Although the invention has been shown and described with respect to a certain preferred embodiment, various alterations and modifications may occur to others skilled in the art upon the reading and understanding of this specification. It is intended that the present invention include all such alterations and modifications and be limited only by the scope of the following claims.

What is claimed is:

1. An intervertebral spacer in the form of a rigid, porous body made of a biocompatible polymer material, the body being strong enough to accommodate loads imposed by adjacent vertebrae and porous enough to facilitate tissue ingrowth and bony fusion, the body including a plurality of randomly sized, substantially interconnected voids that provide porosity throughout the body, wherein the polymer is in the form of pellets that are fused together by sintering.

2. The intervertebral spacer of claim 1, wherein the pellets are in the shape of spherical beads of different sizes.

3. The intervertebral spacer of claim 1, wherein the pellets are made of PEEK resin.

4. An intervertebral spacer in the form of a rigid, porous body made of a biocompatible material of a combination of elongate, tortuous strands and beads, the body being strong enough to accommodate loads imposed by adjacent vertebrae and porous enough to facilitate tissue ingrowth and bony fusion, the body including a plurality of randomly sized, substantially interconnected voids that provide porosity throughout the body, wherein the elongate, tortuous strands and the beads are intermixed and fused by sintering.

5. The intervertebral spacer of claim 4, wherein the elongate, tortuous strands and the beads are selected from the group consisting of titanium, titanium alloys, cobalt-chromium alloys, tantalum, tantalum alloys, niobium, niobium alloys, stainless steel and a polymer.

6. The intervertebral spacer of claim 5, wherein the polymer is PEEK.

7. An intervertebral spacer in the form of a rigid, porous body made of a biocompatible foam metal material, the body being strong enough to accommodate loads imposed by adjacent vertebrae and porous enough to facilitate tissue ingrowth and bony fusion, the body including a plurality of randomly sized, substantially interconnected voids that provide porosity throughout the body, wherein the voids in the foam metal are formed by the steps of:

mixing a blowing agent with powdered metal;

heating the mixture to foaming temperature where voids are formed in the metal; and cooling the void-containing metal.

8. The intervertebral spacer of claim 7, wherein the metal is selected from the group consisting of titanium, titanium alloys, cobalt-chromium alloys, tantalum, tantalum alloys, niobium, niobium alloys, and stainless steel.

9. An intervertebral spacer in the form of a rigid, porous body made of a biocompatible powdered metal material, the body being strong enough to accommodate loads imposed by adjacent vertebrae and porous enough to facilitate tissue ingrowth and bony fusion, the body including a plurality of randomly sized, substantially interconnected voids that provide porosity throughout the body, wherein the voids in the powdered metal are formed by the steps of:

providing powdered metal, a binder, and low melting temperature pellets;

mixing the powdered metal, binder, and pellets;

placing the mixture in a mold;

heating the mixture to a first temperature sufficient to melts the pellets and solidify the binder;

heating the mixture to a second temperature sufficient to oxidize the binder and sinter the powdered metal; and cooling the void-containing metal.

10. The intervertebral spacer of claim 9, wherein the metal is selected from the group consisting of titanium, titanium alloys, cobalt-chromium alloys, tantalum, tantalum alloys, niobium, niobium alloys, and stainless steel.

11. An intervertebral spacer in the form of a rigid, porous body made of a biocompatible ceramic material, the body being strong enough to accommodate loads imposed by adjacent vertebrae and porous enough to facilitate tissue ingrowth and bony fusion, the body including a plurality of randomly sized, substantially interconnected voids that provide porosity throughout the body, wherein the voids in the ceramic are formed by the steps of:

mixing a blowing agent with powdered ceramic;

heating the mixture to foaming temperature where voids are formed in the ceramic; and cooling the void-containing ceramic.

12. The intervertebral spacer of claim 11, wherein the ceramic is selected from the group consisting of alumina, silica, and mixtures of alumina and silica.

13. A method for making an intervertebral spacer, comprising the steps of:

providing a solid block of biocompatible material; and forming a plurality of randomly sized, substantially interconnected voids that provide porosity throughout the body, the voids being created by machining A operations like mechanical, laser, water jet, or plasma drilling, EDM, or chemical attack.

14. The method of claim 13, wherein the block is made from a material selected from the group consisting of titanium, titanium alloys, cobalt-chromium alloys, tantalum, tantalum alloys, niobium, niobium alloys, stainless steel and polymers.

15. The method of claim 14, wherein the polymer is PEEK resin.

16. An intervertebral spacer in the form of a rigid, porous body made of a biocompatible polymer material, the body being strong enough to accommodate loads imposed by adjacent vertebrae and porous enough to facilitate tissue ingrowth and bony fusion, the body including a plurality of randomly sized, substantially interconnected voids that provide porosity throughout the body, the external configuration of the body being defined by:

top and bottom walls, the top and bottom walls being of the same size and shape;

first and second spaced side walls, the side walls being of the same size and shape;

a first end wall; and a second end wall, the second end wall being curved from one side wall to the other side wall, the radius of the curve being constant and approximating the radius of curvature of a vertebral body, wherein the polymer is PEEK resin, and the voids are formed by a machining operation.

17. An intervertebral spacer in the form of a rigid, porous body made of a biocompatible material of spherical beads of different diameters, the body being strong enough to accommodate loads imposed by adjacent vertebrae and porous enough to facilitate tissue ingrowth and bony fusion, the body including a plurality of randomly sized, substantially interconnected voids that provide porosity throughout the body, the external configuration of the body being defined by:
- top and bottom walls, the top and bottom walls being of the same size and shape;
- first and second spaced side walls, the side walls being of the same size and shape;
- a first end wall; and
- a second end wall, the second end wall being curved from one side wall to the other side wall, the radius of the curve being constant and approximating the radius of curvature of a vertebral body, wherein the spherical beads of different diameters are selected from the group consisting of titanium, titanium alloys, cobalt-chromium alloys, tantalum, tantalum alloys, niobium, niobium alloys, stainless steel, and polymer.

18. An intervertebral spacer in the form of a rigid, porous body made of a biocompatible material of tortuous strands and beads, the body being strong enough to accommodate loads imposed by adjacent vertebrae and porous enough to facilitate tissue ingrowth and bony fusion, the body including a plurality of randomly sized, substantially interconnected voids that provide porosity throughout the body, the external configuration of the body being defined by:
- top and bottom walls, the top and bottom walls being of the same size and shape;
- first and second spaced side walls, the side walls being of the same size and shape;
- a first end wall; and
- a second end wall, the second end wall being curved from one side wall to the other side wall, the radius of the curve being constant and approximating the radius of curvature of a vertebral body, wherein the strands and the beads are intermixed and fused by sintering.

19. An intervertebral spacer in the form of a rigid, porous body made of a biocompatible material of tortuous strands and beads, the body being strong enough to accommodate loads imposed by adjacent vertebrae and porous enough to facilitate tissue ingrowth and bony fusion, the body including a plurality of randomly sized, substantially interconnected voids that provide porosity throughout the body, the external configuration of the body being defined by:
- top and bottom walls, the top and bottom walls being of the same size and shape;
- first and second spaced side walls, the side walls being of the same size and shape;
- a first end wall; and
- a second end wall, the second end wall being curved from one side wall to the other side wall, the radius of the curve being constant and approximating the radius of curvature of a vertebral body, wherein the strands and the beads are selected from the group consisting of titanium, titanium alloys, cobalt-chromium alloys, tantalum, tantalum alloys, niobium, niobium alloys, stainless steel, and polymer.

20. An intervertebral spacer in the form of a rigid, porous body made of a biocompatible foam metal material, the body being strong enough to accommodate loads imposed by adjacent vertebrae and porous enough to facilitate tissue ingrowth and bony fusion, the body including a plurality of randomly sized, substantially interconnected voids that provide porosity throughout the body, the external configuration of the body being defined by:
- top and bottom walls, the top and bottom walls being of the same size and shape;
- first and second spaced side walls, the side walls being of the same size and shape;
- a first end wall; and
- a second end wall, the second end wall being curved from one side wall to the other side wall, the radius of the curve being constant and approximating the radius of curvature of a vertebral body, wherein the voids in the foam metal are formed by the steps of:
  - mixing a blowing agent with powdered metal;
  - heating the mixture to foaming temperature where voids are formed in the metal; and
  - cooling the void-containing metal.

21. An intervertebral spacer in the form of a rigid, porous body made of a biocompatible powdered metal material, the body being strong enough to accommodate loads imposed by adjacent vertebrae and porous enough to facilitate tissue ingrowth and bony fusion, the body including a plurality of randomly sized, substantially interconnected voids that provide porosity throughout the body, the external configuration of the body being defined by:
- top and bottom walls, the top and bottom walls being of the same size and shape;
- first and second spaced side walls, the side walls being of the same size and shape;
- a first end wall; and
- a second end wall, the second end wall being curved from one side wall to the other side wall, the radius of the curve being constant and approximating the radius of curvature of a vertebral body, wherein the voids in the powdered metal are formed by the steps of:
  - providing powdered metal, a binder, and low melting temperature pellets;
  - mixing the powdered metal, binder, and pellets;
  - placing the mixture in a mold;
  - heating the mixture to a first temperature sufficient to melts the pellets and solidify the binder;
  - heating the mixture to a second temperature sufficient to oxidize the binder and sinter the powdered metal; and
  - cooling the void-containing metal.

22. An intervertebral spacer in the form of a rigid, porous body made of a biocompatible ceramic material, the body being strong enough to accommodate loads imposed by adjacent vertebrae and porous enough to facilitate tissue ingrowth and bony fusion, the body including a plurality of randomly sized, substantially interconnected voids that provide porosity throughout the body, the external configuration of the body being defined by:
- top and bottom walls, the top and bottom walls being of the same size and shape;
- first and second spaced side walls, the side walls being of the same size and shape;
- a first end wall; and
- a second end wall, the second end wall being curved from one side wall to the other side wall, the radius of the curve being constant and approximating the radius of curvature of a vertebral body, wherein the voids in the ceramic are formed by the steps of:
  - mixing a blowing agent with powdered ceramic;
  - heating the mixture to foaming temperature where voids are formed in the ceramic; and
  - cooling the void-containing ceramic.

23. An intervertebral spacer in the form of a rigid, porous body made of a biocompatible material selected from the group consisting of foam metal and powdered metal, the body being strong enough to accommodate loads imposed by adjacent vertebrae and porous enough to facilitate tissue ingrowth and bony fusion, the body including a plurality of randomly sized, substantially interconnected voids that provide porosity throughout the body, the external configuration of the body being defined by:

top and bottom walls, the top and bottom walls being of the same size and shape;

first and second spaced side walls, the side walls being of the same size and shape;

a first end wall; and a second end wall, the second end wall being curved from one side wall to the other side wall, the radius of the curve being constant and approximating the radius of curvature of a vertebral body, wherein the foam metal and the powdered metal are selected from the group consisting of titanium, titanium alloys, cobalt-chromium alloys, tantalum, tantalum alloys, niobium, niobium alloys, and stainless steel.

24. An intervertebral spacer in the form of a rigid, porous body made of a biocompatible ceramic material, the body being strong enough to accommodate loads imposed by adjacent vertebrae and porous enough to facilitate tissue ingrowth and bony fusion, the body including a plurality of randomly sized, substantially interconnected voids that provide porosity throughout the body, the external configuration of the body being defined by:

top and bottom walls, the top and bottom walls being of the same size and shape;

first and second spaced side walls, the side walls being of the same size and shape;

a first end wall; and a second end wall, the second end wall being curved from one side wall to the other side wall, the radius of the curve being constant and approximating the radius of curvature of a vertebral body, wherein the ceramic is selected from the group consisting of alumina, silica, and mixtures of alumina and silica.

25. An intervertebral spacer in the form of a rigid, porous body made of a biocompatible polymer material, the body being strong enough to accommodate loads imposed by adjacent vertebrae and porous enough to facilitate tissue ingrowth and bony fusion, the body including a plurality of randomly sized, substantially interconnected voids that provide porosity throughout the body, wherein the polymer is in the form of a block of solid material in which the voids are formed by a machining operation.

26. The intervertebral spacer of claim 25, wherein the polymer is PEEK resin.

27. The intervertebral spacer of claim 25, wherein the machining operation is performed by mechanical, laser, water jet, or plasma drilling, EDM, or chemical attack.

* * * * *